(12) United States Patent
Tsoukalis

(10) Patent No.: US 10,100,824 B2
(45) Date of Patent: Oct. 16, 2018

(54) PULSELESS ROTARY PERISTALTIC PUMP

(71) Applicant: MICREL Medical Devices S.A., Gerakas (GR)

(72) Inventor: Achilleas Tsoukalis, Anavyssos Attiki (GR)

(73) Assignee: Micrel Medical Devices S.A., Gerakas (GR)

( * ) Notice: Subject to any disclaimer, the term of this patent is extended or adjusted under 35 U.S.C. 154(b) by 214 days.

(21) Appl. No.: 14/931,460

(22) Filed: Nov. 3, 2015

(65) Prior Publication Data

US 2016/0123320 A1     May 5, 2016

(30) Foreign Application Priority Data

Nov. 4, 2014   (EP) .................................. 14191769

(51) Int. Cl.
 *F04B 43/12*   (2006.01)
 *A61M 5/142*   (2006.01)
(52) U.S. Cl.
 CPC ..... *F04B 43/1253* (2013.01); *A61M 5/14232* (2013.01); *A61M 2205/12* (2013.01); *A61M 2205/502* (2013.01)
(58) Field of Classification Search
 CPC ... F04B 43/12; F04B 43/1253; F04B 43/1276
 See application file for complete search history.

(56) References Cited

U.S. PATENT DOCUMENTS 3,826,593 A   7/1974  Von Casimir
5,230,614 A   7/1993  Zanger et al.
5,470,211 A  11/1995  Knott et al.
5,533,878 A   7/1996  Iwata
7,654,127 B2  2/2010  Krulevitch et al.
 (Continued)

FOREIGN PATENT DOCUMENTS

EP   2708251    3/2014
GB   2076068   11/1981

OTHER PUBLICATIONS

EP Search Report for EP App. No. 15192838.9 dated Mar. 3, 2016, 8 pages.

*Primary Examiner* — Patrick Hamo
(74) *Attorney, Agent, or Firm* — Hollingsworth Davis, LLC

(57) ABSTRACT

An infusion pump comprises peristaltic pump means with tubing comprising four zones. The first, most upstream, zone provides for an engagement element to engage the tubing during movement along the first zone, and the engagement element remains in engagement with the tubing during movement along the second and third zones. The fourth, most downstream, zone provides for an engagement element to disengage from the tubing during movement along the fourth zone. The length of each of the zones is shorter than the distance between the two neighboring engagement elements, and the sum of the second and third zone lengths is equal to the distance between the two neighboring engagement elements. The second zone cross-section is larger than the third zone cross-section, leading to a volume increase which is at least equal to a volume increase displaced in the fourth zone resulting from disengagement of an engagement element from the tubing.

16 Claims, 9 Drawing Sheets

(56) References Cited

U.S. PATENT DOCUMENTS

| | | | | |
|---|---|---|---|---|
| 7,722,338 B2* | 5/2010 | Nordell | ............... | F04B 43/1253 417/477.11 |
| 2006/0245964 A1* | 11/2006 | Koslov | ............... | F04B 43/1253 417/477.1 |

* cited by examiner

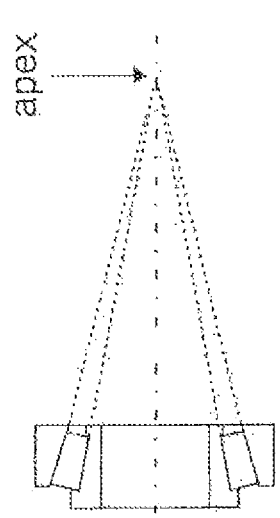
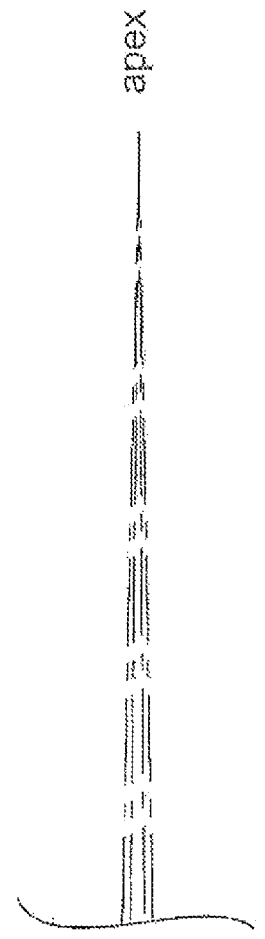
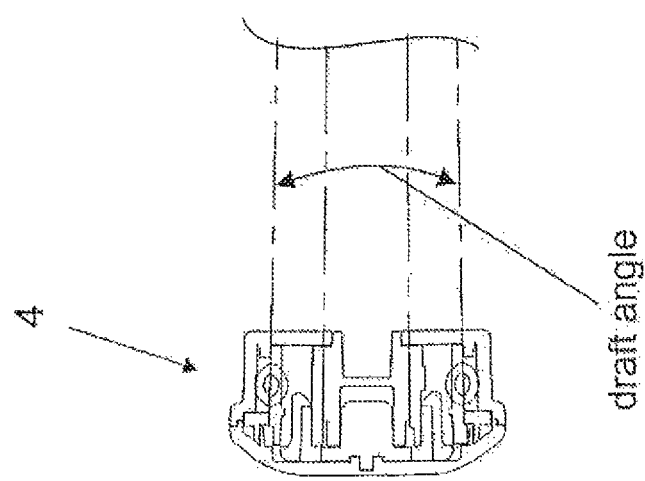
Fig. 9b
Fig. 9a

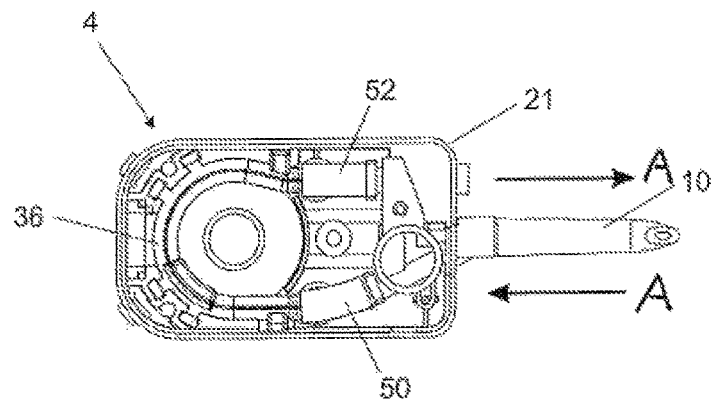
Fig. 10a
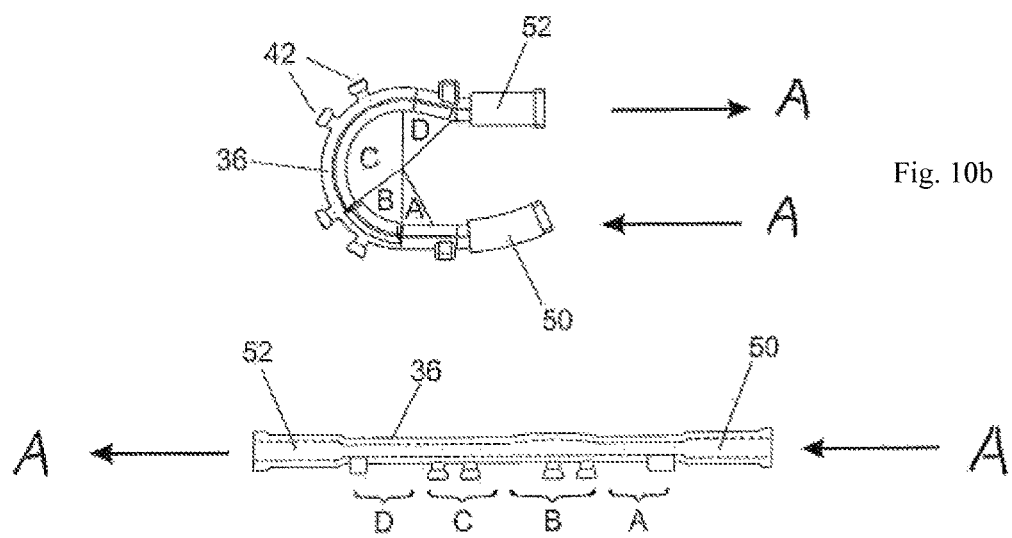
Fig. 10b
Fig. 10c

PULSELESS ROTARY PERISTALTIC PUMP

FIELD OF THE INVENTION

The present invention relates to an infusion pump device comprising a peristaltic pump means including a stationary flexible, preferably resilient, tubing which has an inlet and an outlet and is provided to accommodate a fluid flowing in downstream direction from the inlet to the outlet, and at least two engagement elements which are spaced from each other by a predetermined constant distance and provided to locally engage with the tubing and to be repeatedly moved along the tubing in downstream direction so as to locally squeeze the tubing for a pump action during movement along the tubing and to encapsulate a volume of the tubing between the neighboring engagement elements.

BACKGROUND OF THE INVENTION

In medical practice, syringe pumps are used for drugs which need high accuracy and have a short half-life in the body. In operating theatres and intensive care units, syringe pumps are mounted in stacks of in particular six to eight pumps that, however, require a lot of space and allow only low visibility and recognition of the indication of a drug provided on the syringe. Apart from occupation of large space syringe pumps have more problems, since a nominal trumpet curve and, thus, a constancy index cannot be achieved in practice due to the fact that the plunger usually made of rubber sticks to the walls of the syringe and therefore advances in pulses rather than continuously. Further, syringe pumps also have low sensitivity in occlusion pressure reading, that becomes a problem in neonatal infusions and recently with the use of wearable bolus large volume injectors. Syringe pumps are extensively used mainly in Europe, where about 40% of the beds in each hospital are equipped with a syringe pump, and for insulin infusions and most of immunoglobulin and Parkinson's disease infusions. It has been proposed to replace insulin syringe pumps by diaphragm pumps that, however, cannot be realized in practice since insulin crystallizes and renders active and passive valves of the mechanism leak.

Pre-filled syringes are part of a growing pharmaceutical delivery sector and work well for injections, but are problematic for longer term infusions, since they become bulky especially for newer biological drugs and have a volume limit of about 60 to 100 ml. So, the pumps become bulky as the needed infusion volume increases.

Syringe pumps are used because prior art peristaltic pumps had a low accuracy and causes a pulsatile flow and, hence, not a linear flow per infusion cycle, wherein during a part of the cycle there is no infusion but sometimes even a backflow, so that their constancy index is high for short half-life drugs. Short-term accuracy can be expressed by the concept of constancy index. This is the shortest period during a steady-state operation of a pump over which a measurement of output consistently falls within +/−10% of the mean rate. These data are derived from flow tests performed over 24 hours at 1 ml/h, wherein the flow is recorded at 30 seconds intervals during the final 18 hours period and the average rate is compared with the flow over each short period.

Peristaltic pumps comprise a housing and a compressible tubing arranged within the housing. Basically, there are two different embodiments of the peristaltic pump, wherein in the one embodiment the tubing is arranged along a straight track, whereas in the other embodiment the tubing is formed as a loop resulting in a more economical design with a smaller physical size and less producing costs. The former embodiment which is called a linear peristaltic pump is mainly used nowadays, while the present invention deals with the latter embodiment. The tubing is to be filled with a fluid to be delivered from its inlet to its outlet. The fluid is caused to move through the tubing by engagement elements, typically in the form of rollers driven by rotary means such an electric motor or a mechanically driven shaft. The engagement elements cause an occlusion of the tubing by squeezing it against a wall or track within the housing so that the fluid is forced through the tubing due to the movement of the engagement elements. The use of a peristaltic pump is advantageous in so far as the fluid does not come into contact with the operating environment, which renders the peristaltic pump suitable for medical applications like infusion of drugs where it is important to avoid contact of the fluid with the environment. Further, the mechanical components of a peristaltic pump do not come into contact with the fluid. So, the components of a peristaltic pump remain free from contamination by the fluid. As a result, a peristaltic pump is easy to clean and to sterilize because the tubing can be simply discarded after use, and a new tubing can be provided for the next use.

However, a disadvantage is that it is difficult with a peristaltic pump to achieve a constant or pulseless flow of the fluid through the tubing. Pulses are created when the engagement elements disengage from the tubing and, therefore, the occlusion is removed with the result of that a void is generated in the disengagement region of the tubing. Namely, in this region the tubing returns to its normal round shape resulting in an increase of the volume which are filled by fluid from the outlet of the tubing. This leads to a reduction of the flow rate of the fluid at the outlet of the tubing for the duration of the pulse.

In other words, the pulsatile behavior of a rotary peristaltic pump results from the alternation of a forerunner or leading engagement element by the next follower or trailing engagement element. V is the volume which is encapsulated between two neighboring engagement elements. In case of a rotary peristaltic pump, with $\varphi$ defining an angular position so that the angular position of the trailing engagement element is $\varphi 1$ and the angular position of the leading engagement element is $\varphi 2$, the volume V encapsulated between both these engagement elements extends along an angular distance which is defined by the difference between both the aforementioned angular positions $\varphi 2$ and $\varphi 1$, i.e. $\Delta\varphi = \varphi 2 - \varphi 1$. $+\Delta V/\Delta\varphi$ represents an increase of the volume defining a so-called frontwave which is displaced in front of each engagement element and is advanced by it. $-\Delta V/\Delta\varphi$ represents a decrease of the volume defining a so-called depression which arises behind each engagement element. The enclosed volume V between two neighboring engagement elements squeezing the tubing with unchanged distance between them is constant so that the fluid is just transported, if $+\Delta V/\Delta\varphi$ and $-\Delta V/\Delta\varphi$ are the same so that $$V + \Delta V/\Delta\varphi - \Delta V/\Delta\varphi = V,$$

resulting in that the pressure remains constant as well.

If otherwise an upstream portion of the tubing is larger than a downstream portion so that it is $$\Delta V_2/\Delta\varphi > \Delta V_1/\Delta\varphi \text{ and}$$

$$V + \Delta V_2/\Delta\varphi - \Delta V_1/\Delta\varphi = V + V\text{difference},$$

wherein $\Delta V_1/\Delta\varphi$ represents an increase of volume defining a front wave in front of the forerunner or leading engagement element and $\Delta V_2/\Delta\varphi$ represents an increase of volume defining a front wave in front of the next follower or trailing engagement element, the pressure is increased by elastic tubing forces of the inflated portion due to increase of volume.

At the moment the leading engagement element stops squeezing the tubing and a front/back communication through a thin film of fluid is established under it, the frontwave $+\Delta V/\Delta\varphi$ suddenly disappears (so that it cannot push fluid anymore) and is replaced by the frontwave in front of the trailing engagement element which now takes over relay of infusion. Also $-\Delta V/\Delta\varphi$ disappears behind it. But due to the disengagement of the leading engagement element a new additional difference volume $\Delta Vd/\Delta\varphi$ is built up and continues to be present until the disengagement of the leading engagement element is fully completed. A void creating the aforementioned new additional volume difference $\Delta V_d$ arises, as the resilient tubing becomes asymptotic or starts with a larger diameter disengagement curvature at this point, resulting in a creation of a negative pulse $\Delta V/\Delta\varphi - \Delta Vd/\Delta\varphi$ in the flow graph $(V,\varphi)$ (where $\Delta Vd$ depends on the geometry of the engagement element and the disengagement curvature $\Delta r/\Delta\varphi$ of the housing and r is the radius of the disengagement curvature increasing so as to let the engagement element disengage).

The flow rate is defined as $\Delta V/\Delta t$. By multiplying the nominator and the denominator each with $\Delta\varphi$, the above equation can be written as $$\text{flow rate} = (\Delta V/\Delta\varphi) \cdot (\Delta\varphi/\Delta t).$$

This makes evident that for a constant rotational movement $\Delta\varphi/\Delta t$, if $\Delta V$ is constant at the vicinity of an engaging element at any location along its movement path, the flow rate will be constant without any variation or pulse.

The lack of a constant fluid caused by pulses in the tubing renders a peristaltic pump unsuitable for certain precision applications. E.g., in applications where a small volume of fluid is required, such as where less than a complete revolution of the rotor is used, the effect of the pulses are particularly disadvantageous.

U.S. Pat. No. 5,533,878 A discloses a squeeze type pump wherein the resilient tubing has a larger diameter at the start of an infusion cycle than at its end.

U.S. Pat. No. 7,654,127 B2 discloses a peristaltic pump with increased dimensions in an upstream portion of the tubing so as to increase pressure inside the tubing before disengagement of a roller squeezing the tubing. However, the pressure is suddenly released when the leading roller is going to be disengaged from the tubing. Therefore, a perturbation of flow happens first with a sudden increase of flow and second with a decrease of it at same quantity due to disengagement of the roller from the tubing after some rotational degrees.

U.S. Pat. No. 3,826,593 A proposes the provision of a cam compressing the tubing at another point at the same time the engagement roller is disengaged from the tubing in a peristaltic pump. However, this solution requires higher costs and a larger number of assembly parts and is therefore not suitable for a disposable pumping mechanism.

U.S. Pat. No. 5,470,211 A teaches a roller pump with the provision of a controlled curvature at the inlet and the outlet of the tubing.

It is an object of the present invention to provide a continuously operating pulseless and accurate peristaltic pump having a small size so that it can replace many bulky syringe pumps in limited space.

SUMMARY OF THE INVENTION

In order to achieve the above and further objects, according to the present invention, there is provided an infusion pump device, comprising a peristatic pump means including
  a stationary flexible, preferably resilient, tubing which has an inlet and an outlet and is provided to accommodate a fluid flowing in downstream direction from the inlet to the outlet, and
  at least two engagement elements which are spaced from each other by a predetermined constant distance and provided to locally engage with the tubing and to be repeatedly moved along the tubing in downstream direction so as to locally squeeze the tubing for a pump action during movement of the engagement element along the tubing and to encapsulate a volume of the tubing between two neighboring engagement elements,
  wherein the tubing comprises first to fourth zones directly joining each other in downstream direction,
  wherein the first zone being the most upstream zone is provided so that an engagement element comes into engagement with the tubing during movement along the first zone,
  wherein the second and third zones are provided so that an engagement element remains in engagement with the tubing during movement along the second and third zones,
  wherein the fourth zone being the most downstream zone is provided so that an engagement element is disengaged from the tubing during movement along the fourth zone,
  wherein the length of each of the zones is shorter than the distance between the two neighboring engagement elements,
  wherein the sum of the lengths of the second and third zones is equal to the distance between the two neighboring engagement elements, and
  wherein the cross-section of the second zone is larger than the cross-section of the third zone by an amount leading to an increase of volume which is at least equal to an increase of volume displaced in the fourth zone resulting from the disengagement of an engagement element from the tubing.

Preferred embodiments and modifications are defined in the dependent claims.

Preferably, the length of the second zone is equal to the length of the fourth zone.

Preferably, the sum of the lengths of the second and third zones is equal to the distance between the two neighboring engagement elements.

Preferably, the sum of the lengths of the third and fourth zones is equal to the distance between the two neighboring engagement elements.

Preferably, the length of the third zone is longer than the length of the first zone and/or of the second zone and/or of the fourth zone.

Preferably, the cross-section of the first zone is larger than the cross-section of the third zone, in particular in case the working pressure downstream is relatively high.

Preferably, there are provided a housing accommodating the peristaltic pump means, and fixing means for fixing the tubing to the housing so as to prevent movement of the tubing relative to the housing, resulting in an increase of the accuracy in order to improve repeatability of the process.

According to a modification of this embodiment the fixing means can be provided as anchors and/or adapted to fix the tubing to an inner wall of the housing.

According to a further preferred embodiment, the peristaltic pump means is a rotary peristaltic pump means comprising a rotor which is provided with the engagement elements wherein the tubing comprises a bent portion having an essentially part-cycle form, wherein the length of the zones is represented by an angular distance.

According to a preferred modification of the aforementioned embodiment, the angular distance of the first zone is up to 15°.

According to a preferred modification of the aforementioned embodiment, the angular distance of the second zone is 20° to 60°.

According to a further preferred modification of the aforementioned embodiment, there are two engagement elements which are arranged essentially diametrically opposite to a rotary axis of the rotor, wherein the sum of the angular distances of the second and third zones is equal to 180°.

According to an alternative modification, there are three engagement elements which are spaced from a rotary axis of the rotor by the same radial distance wherein two neighboring engagement elements each are spaced from each other by an angular distance of 120°, wherein the sum of the angular distances of the second and third zones is equal to 120°.

According to a further preferred modification of the aforementioned embodiment, the engagement elements are provided as engagement rollers.

According to a preferred modification, the rotor comprises a central roller which is in frictional engagement with the engagement rollers.

According to a further preferred modification of the aforementioned embodiment, there are provided
- a housing which is divided into at least three operating layers positioned one above the other, wherein
- an epicyclic gear layer includes an epicyclic gear means comprising a rotatable central gear, a stationary outer ring gear surrounding the central gear, and movable planet gears which are arranged between the central gear and the ring gear and in movable engagement with both the central gear and the ring gear,
- a bearing layer includes a roller bearing means comprising a stationary outer ring and a movable inner roller arrangement which is in movable arrangement with the outer ring and coupled with the epicyclic gear means so as to provide a rotational bearing for the central and planet gears and
- a pumping operating layer includes the rotary peristaltic pump means wherein the rotor is coupled with the central gear of the epicyclic gear means so that a torque is transferred from the central gear to the rotor.

According to a preferred modification, the rotor is non-rotatably coupled in coaxial arrangement with the central gear of the epicyclic gear means.

According to a further preferred modification, the inner roller arrangement of the roller bearing means is non-rotatably coupled with at least the central gear of the epicyclic gear means.

According to a further preferred modification, the inner roller arrangement of the roller bearing means comprises a rotatable central roller and movable planet rollers which are arranged between the central roller and the outer ring and in movable frictional engagement with both the central roller and the outer ring.

According to a further preferred modification, the central gear of the epicyclic gear means is non-rotatably coupled in coaxial arrangement with the central roller of the roller bearing means.

According to a further preferred modification, at least one of the planet gears of the epicyclic gear means is non-rotatably coupled in coaxial arrangement with one of the planet rollers of the roller bearing means.

According to a further preferred modification, the roller bearing means comprises two planet rollers which are arranged essentially diametrically opposite to the rotary axis of the central roller.

According to a further preferred modification, the epicyclic gear means comprises two planet gears which are arranged essentially diametrically opposite to the rotary axis of the central gear.

According to a further preferred modification, at least one of the engagement rollers is non-rotatably coupled in coaxial arrangement with one of the planet gears of the epicyclic gear means.

According to a preferred modification, the rotor of the rotary peristaltic pump means comprises a central roller which is in frictional engagement with the engagement rollers and is non-rotatably coupled in coaxial arrangement with the central gear of the epicyclic gear means.

According to a preferred modification, the gear ratio between the planet gears and the central gear of the epicyclic gear means corresponds to the ratio between the diameter of the engagement rollers and the diameter of the central roller of the rotor of the rotary peristaltic pump means.

Preferably, the central gear of the epicyclic gear means, the central roller of the roller bearing means and the central roller of the rotor of the rotary peristaltic pump means are commonly formed as an integral central rotary body, and/or wherein at least a planet gear of the epicyclic gear means, a planet roller of the roller bearing means and an engagement roller of the rotor of the rotary peristaltic pump means are commonly formed as an integral planet rotary body.

According to a further preferred embodiment, the housing includes a bent wall portion supporting at least a portion of the tubing and providing the tubing with a curved shape, and the engagement roller(s), the central roller, the outer ring and the bent wall portion comprise a slight conical shape in the same direction so that their surfaces intercept at a single point.

According to a further preferred embodiment, there is provided a shutter means which is adapted to be optionally placed either in a first position or in a second position, wherein the shutter means in its first position allows the tubing to be squeezed by an engagement element for pumping action and in its second position prevents the tubing from squeezing by an engagement element so as to let air or fluid pass through the tubing.

According to a preferred embodiment, there is provided a controlling means for controlling the movement of the engagement elements so as to correct the position and speed of the engagement elements if needed.

Preferably, the cross-section of the tubing in all the four zones is elliptical or has a shape similar to an arrangement of two parentheses facing each other like "( )" resulting in a reduction of the power needed.

BRIEF DESCRIPTION OF THE DRAWINGS

Preferred embodiments of the present invention will now be described with reference to the drawings, in which:

FIGS. 9a-b schematically indicate that the pump cartridge and its inner components comprise a slide conical shape;

FIGS. 10a-c schematically show the configuration of the tubing and its division into four zones according to a preferred embodiment, by illustrating a longitudinal section through the pump cartridge at the level of the pumping layer in (a), a single view of the tubing in its curved configuration from above (b), and a single view of the tubing in a straightened condition for a better understanding (c);

DESCRIPTION OF PREFERRED EMBODIMENTS

Figure 1A:
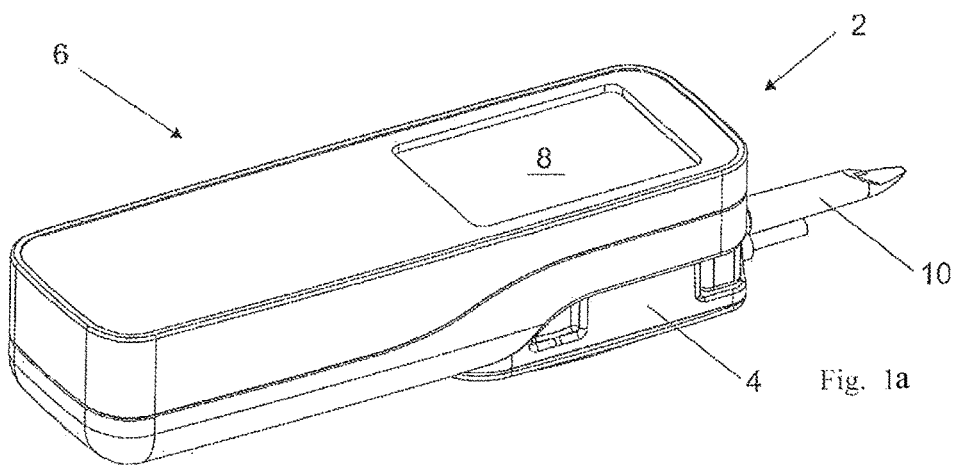
FIGS. 1a-b show a perspective front view (a) and a perspective rear view (b) of a pump according to a preferred embodiment.
Figure 1B:
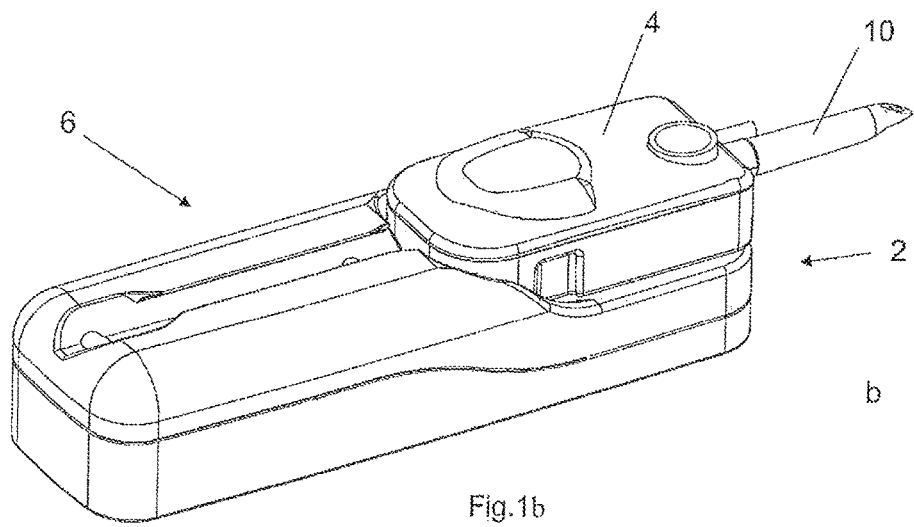

In FIG. 1, there is shown a pump 2 according to a preferred embodiment. In the shown embodiment, the pump 2 is divided into two parts, i.e. a first part 4 including a rotary peristaltic pump mechanism, and a second part 6 only including a motor for driving the pump mechanism in the first part 4 and further hardware like control and detection electronics (not shown). According to the shown embodiment, the first part 4 defines a consumable pump cartridge 4 which is preferably made of plastic resulting in low manufacturing costs and low weight. The second part 6 defines the rest of the pump 2 and is called a pump module 6. The pump module 6 comprises a display 8 shown in FIG. 1a and keys (not shown) at its front side for a convenient use and control. As shown in FIG. 1b, the pump cartridge 4 is fastened at the rear side of the pump module 6.

Figure 2A:
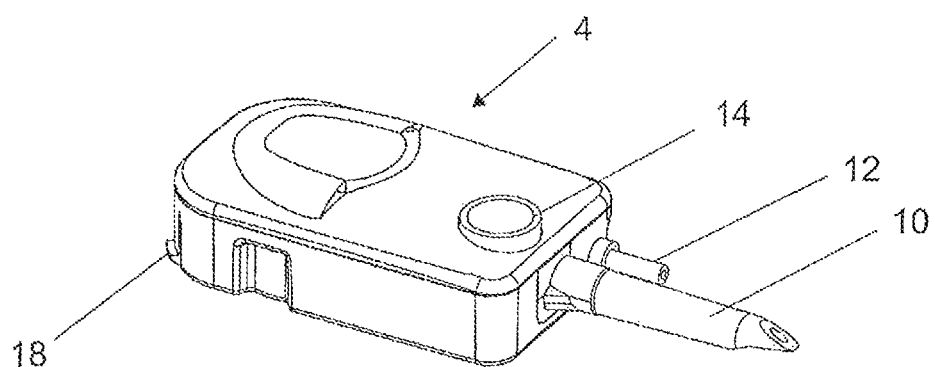
FIGS. 2a-b show a perspective front view (a) and a perspective rear view (b) of a pump cartridge according to a preferred embodiment.

In FIG. 2, the pump cartridge 4 including the rotary peristaltic pump mechanism is shown in greater detail. The pump cartridge 4 is provided with a spike 10 which defines an inlet port. The spike 10 is provided to be put preferably into an outlet port of a medication reservoir (not shown) or into an downstream end of an upstream tube (not shown) so as to create a fluid connection between the medication reservoir and the pump cartridge 4. Further, the pump cartridge 4 is provided with an outlet connector 12 which defines an outlet port and is provided to be put into an upstream end of a downstream tube (not shown). Both the aforementioned tubes (not shown) are part of an infusion line leading from the medication reservoir via the rotary peristaltic pump means in the pump cartridge 4 to a patient. So, the fluid flowing along said infusion line enters the rotary peristaltic pump mechanism within the pump cartridge 4 through the spike 10 and exit it through the outlet connector 12. As to be further seen from FIG. 2, the pump cartridge 4 comprises at the one side being a front side a spike air vent 14 and at the other side being the rear side a motor coupling element 16 to be driven by the motor included in the pump module 6. Moreover, the pump cartridge 4 comprises at its rear side fastening means 18 by which the pump cartridge 4 is attached with its rear side to the rear side of the pump module 6 as shown in FIG. 1. With the pump cartridge 4 being attached to the pump module 6, a coupling between the motor in the pump module 6 and the motor coupling element 16 at the rear side of the pump cartridge 4 is created so that the rotary peristaltic pump mechanism within the pump cartridge 4 is driven by the motor of the pump module 6.

Figure 3:
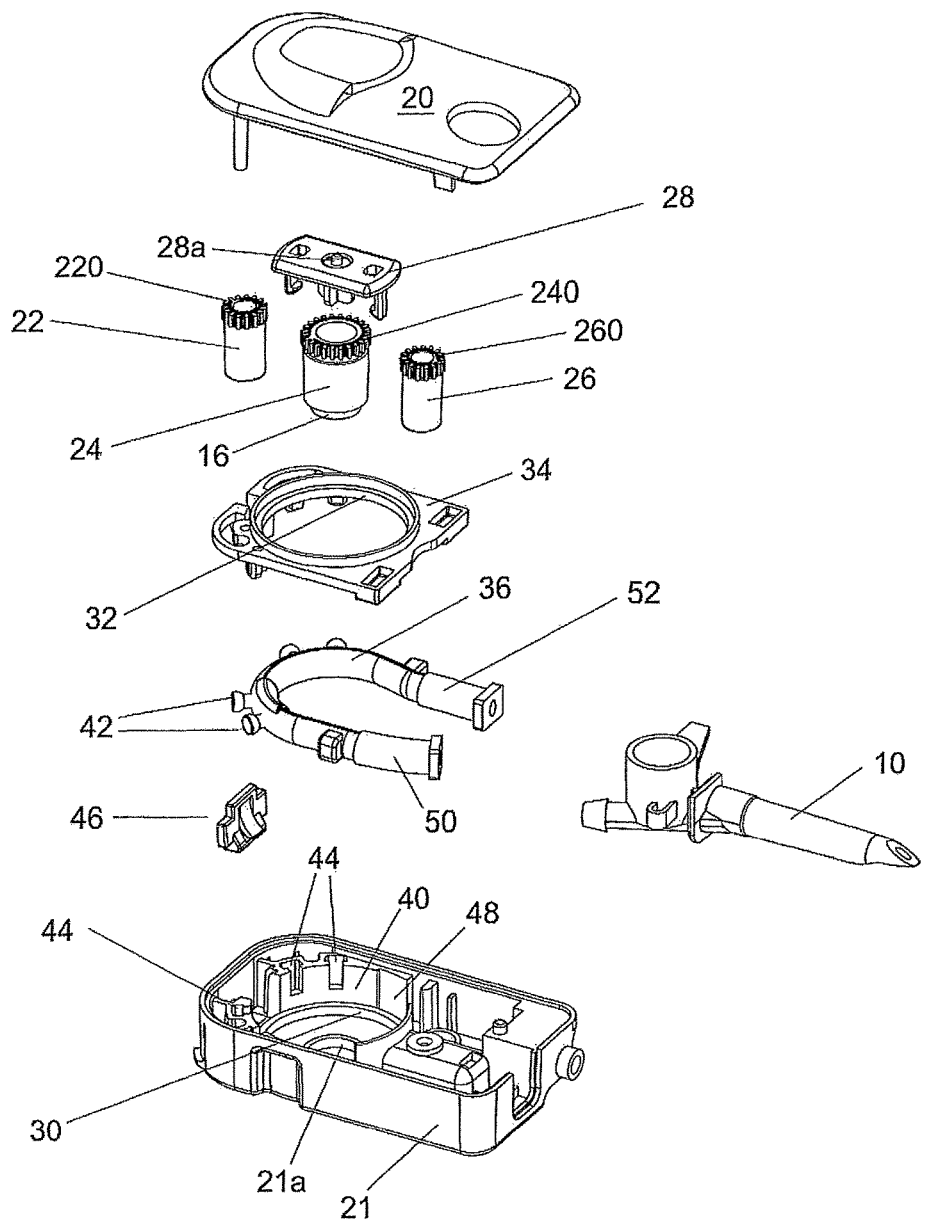
FIG. 3 shows an exploded perspective view of the pump cartridge of FIG. 2.
Figure 4:
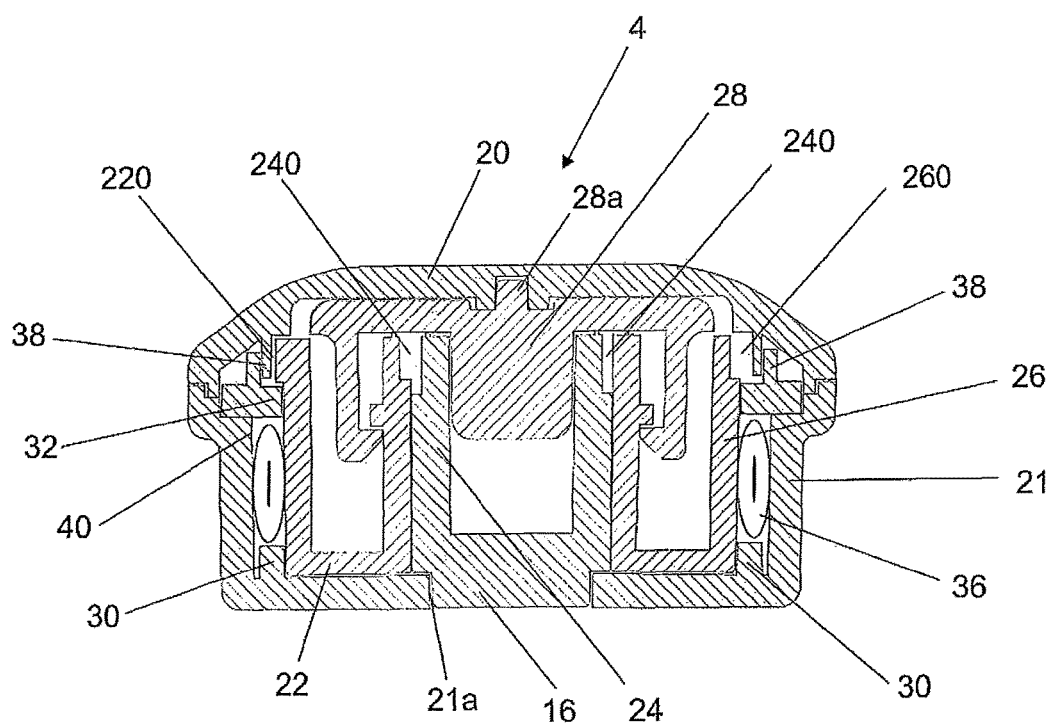
FIG. 4 shows a (vertical) cross-section view through the pump cartridge of FIG. 2.

As detailed in particular in FIGS. 3 and 4, the pump cartridge 4 according a preferred embodiment has two snap-fitting lower and upper parts 20, 21 of a housing in which all other mechanism parts are included wherein the lower and upper parts 20, 21 define lower and upper covers of the housing and therefore commonly form the housing itself. Three cylindrical rollers 22, 24, 26 each having a gear 220, 240, 260 provided at its upper part according to the view of the FIGS. 3 and 4, are used as combined driving and pumping elements, and include two planet rollers 22, 26 of same diameter and one central or sun roller 24, wherein all the cylindrical rollers 22, 24, 26 are arranged in the same (rotating) plane with their rotational axes oriented side by side in the same plane and the gear/diameter ratio of the central or sun gear 240 of the central or sun roller 24 to the planet gears 220, 260 of the planet rollers 22, 26 determines the reduction ratio of the rotation of the planet rollers 22, 26 over the rotation of the central or sun roller 24.

Figure 2B:
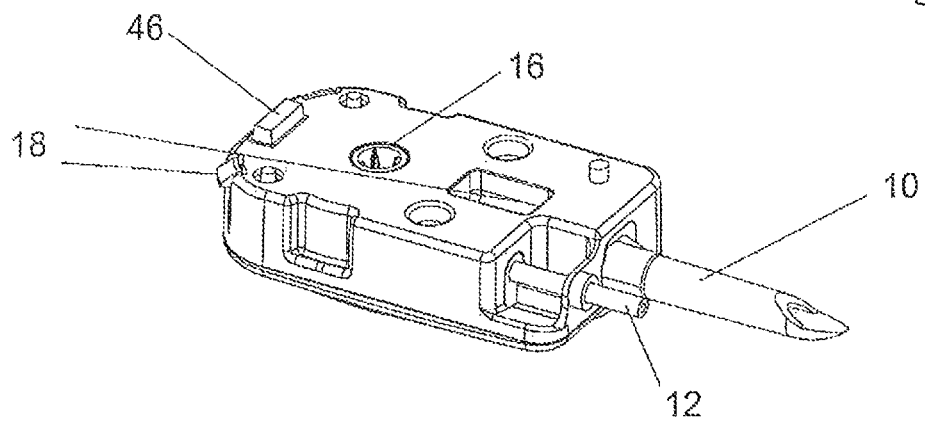

In the illustrated embodiment, there is provided a gear holder 28 which rotatably supports the planet rollers 22, 26 and the central roller 24. The gear holder 28 is provided as a rotor and rotatable about a rotational axis which coincides with the rotational axis of the central roller 24. As to be seen from the FIGS. 3 and 4, the top of the gear holder 28 is provided with a center pin 28a which loosely extends into a recess configured at the inner side of the upper part 20 of the housing, and the opposite lower end or bottom of the central roller 24 is provided with a central cylindrical protrusion which defines the aforementioned motor coupling element 16 as also shown in FIG. 2b and loosely extends through an opening 21a configured in the bottom of the lower part 21 of the housing. Since the central pin 28a is loosely arranged within the recess and the cylindrical motor coupling element 16 is loosely arranged within the opening 21, a larger play is created resulting in an easy rotational movement of the gear holder 28 and the central roller 24. However, for functional reasons such a gear holder 28 is not required since the whole pump 2 works fine without it, but the provision of such a gear holder 28 might be recommendable for safety reasons in particular in case teeth of the gears 220, 240, 260 are damaged or even missing.

Preferably, a small cylindrical magnet may be provided in one of the planet rollers 22, 26 so as to define a roller position and to give that the planet rollers 22, 26 are rotating at a predetermined rated speed which is measured by a Hall sensor placed in the pump module 6 for safety and motor speed control reasons.

Figure 5:
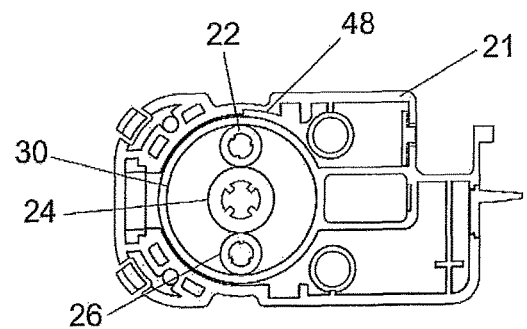
FIG. 5 shows a (horizontal) longitudinal section through the pump cartridge of FIG. 2 at a level of a first bearing layer.

A first outer bearing ring 30 is formed in the lower part 21 of the housing to be arranged within the housing, and a second outer bearing ring 32 is formed in an insert 34 which is arranged within the lower part 21 of the housing. The planet rollers 22, 26 roll inside along the first and second outer bearing rings 30, 32, wherein the first outer bearing ring 30 defines a first bearing stage or layer as also shown in FIG. 5 and the second outer bearing ring 32 defines a second bearing stage or layer as also shown in FIG. 7. The planet rollers 22, 26 further extend through a pumping stage or layer shown in FIG. 6 for rolling along a resilient tubing 36 and squeezing it which tubing is arranged in the pumping layer and accommodated in a cavity of the lower part 21 of the housing having a "Π"-shaped cross-section as shown in particular in the FIGS. 3 and 4. Adjacent to the upper part 20 of the housing there is a gear stage or layer comprising an outer annulus gear ring 38 which is molded in the lower part 21 of the housing and shown in FIG. 8 as well as the aforementioned two planet gears 220, 260 and the central or sun gear 240 which commonly form an epicyclic gear, as per se known in the prior art, wherein the central gear 240 creates a rotating moment onto the planet gears 220, 260 against the outer gear ring 38. The two planet rollers 22, 26 and the central roller 24 are all three in contact with each other and roll on each other so that the resilient tubing 36 included in the aforementioned cavity is squeezed by the planet rollers 22, 26, as schematically shown in FIG. 4. When doing so, radial forces are compensated and, hence, eliminated by the bearing in the two roller bearing layers.

The tangential component of the forces results in a rotating moment and, hence, a torque around the central or sun gear 240 equal to the torque in the central or sun roller 24 and driven via the motor coupling element 16 (cf. FIG. 2b) by a motor (not shown) included within the pump module 6 (cf. FIG. 1). Such torque makes the rollers 22, 24, 26 rotate for a peristaltic infusion.

Figure 6:
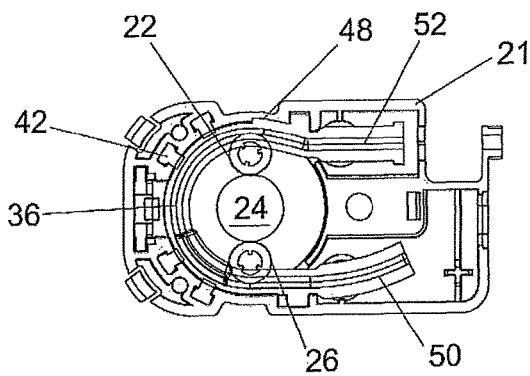
FIG. 6 shows a (horizontal) longitudinal section through the pump cartridge of FIG. 2 at a level of a pumping layer.
Figure 7:
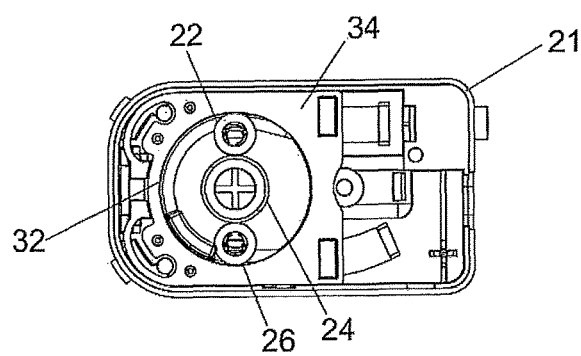
FIG. 7 shows a (horizontal) longitudinal section through the pump cartridge of FIG. 2 at a level of a second bearing layer.

As in particular shown in FIGS. 3 and 6, the aforementioned cavity in the lower part 21 of the housing forms a barrel and is limited by a curved or bent wall portion 40 against which the tubing 36 is laid so that the shape of the portion of the tubing 36 which is in contact with the curved or bent wall portion 40 is determined by the curved or bent shape of the wall portion 40; so, the tubing 36 gets a curved or bent portion as shown in the FIGS. 3 and 6. As to be seen from FIG. 4, the aforementioned cavity of the lower part 21 of the housing having a "Π"-shaped cross-section is limited by the two bearing rings 30, 32 and the wall portion 40. As further to be seen from the FIGS. 3 and 4, the radial depth of the cavity is smaller than the thickness of the tubing 36 in the uncompressed state.

The tubing 36 is fixed both tangentially and radially to the curved or bent wall portion 40 of the lower part 21 of the housing by means of hooks 42 provided along the periphery of the tubing 36 and to be inserted into corresponding recesses 44 provided in the wall portion 40 as in particular shown in the FIGS. 3 and 6. So, it is not possible that the tubing 36 is pulled and extended during the rolling movement of the planet rollers 22, 26.

As further shown in FIG. 3, a part of the curved wall portion 40 in the lower part 21 of the housing is interrupted by a recess into which a shutter 46 is accommodated. The shutter 46 is movable between a first or closed position and a second or opened position. In its first or closed position the shutter 46 forms a continuing part of the curved wall portion 40 wherein the tubing 36 is accommodated so that the tubing 36 can be squeezed by the planet rollers 22, 26. In its second or opened position, the shutter 46 is arranged so that in the region thereof the tubing 36 cannot be squeezed but is enabled to be relaxed and unstressed so that, in particular for sterilization purposes, air or fluid is allowed to freely pass through the tubing 36 where the pump 2 and hence the rotary peristaltic pump mechanism within the pump cartridge 4 is not working and a planet roller 22 or 26 is placed in the region of the shutter 46. The shutter 46 is configured and arranged so that it is moved into its first or closed position by a press action when the pump cartridge 4 is attached to the pump module 6 (cf. FIG. 1). Further, the shutter 46 is arranged and configured so that it remains in its first or closed position when the pump cartridge 4 is released from the pump module 6 in order to prevent free flow.

So, the rotary peristaltic pumping mechanism according to the preferred embodiment as illustrated has four operating stages or layers over its height. A preferred implementation as shown has a first operating layer defining a first bearing layer including a first roller bearing arrangement provided by the planet rollers 22, 26, the central or sun roller 24 and the first outer bearing ring 30, a second layer which is a pumping layer including a rotary peristaltic pump means provided by the planet rollers 22, 26, the central or sun roller 24, the tubing 36 and the wall portion 40, a third layer which defines a second bearing layer including a second roller bearing arrangement provided by the planet rollers 22, 26, the central or sun roller 24 and the second outer bearing ring 32 and finally a fourth layer which defines an epicyclic gear layer provided by the planet gears 220, 260, the central or sun gear 240 and the outer gear ring 38. Due to this arrangement, a proper distribution of forces in the bearings are achieved, wherein the cavity of the lower part 21 of the housing accommodating the tubing 36 comprises the aforementioned "Π"-shaped cross section with its height being limited by the outer bearing rings 30, 32 of the bearing layers and with its radial width being limited by the curved wall portion 40, for a complete squeezing of the tubing 36, as shown in FIG. 4, to a maximum pressure as needed from the pump.

FIG. 5 shows the first bearing layer comprising the driving cylindrical central or sun roller 24 and the planet rollers 22, 26 which are in contact with the central or sun roller 24 and the first outer bearing ring 30 forming a 360° annulus, which assures as in all bearings that when squeezing the tubing 36 the counterforces against the planet rollers 22, 26 cause a force reaction at the bearing parts of all the three rollers 22, 24, 26 in line and, hence, are compensated and eliminated against each other. So, there is no friction in the rotational axes (not shown) of the rollers 22, 24, 26 since it is therefore not subject to any radial force resulting in a reduction of the battery consumption compared to the prior art. Due to the compensation of the counter forces, an omission of the central pin 28a at the top of the gear holder 28 might be alternatively considered.

FIG. 6 shows a second layer defining the pump layer which does not comprise a body or barrel which is closed around 360° as in the remaining layers, but is open at about 170°, wherein each planet roller 22, 26 works as a pump rotary peristaltic roller squeezing the resilient tubing 36 against the outer wall portion 40 of the lower part 21 of the housing as shown in FIG. 4.

FIG. 7 shows a second bearing layer comprising the driving cylindrical central or sun roller 24 and the planet rollers 22, 26 which are in contact with the central or sun roller 24 and the second outer bearing ring 32 forming a 360° annulus, which assures as in all bearings that when squeezing the tubing 36 the counterforces against the planet rollers 22, 26 cause a force reaction at the bearing parts of all the three rollers 22, 24, 26 in line and, hence, are compensated and eliminated against each other. So, there is no friction in the rotational axes (not shown) of the three rollers 22, 24, 26 since they are therefore not subject to any radial force.

Figure 8:
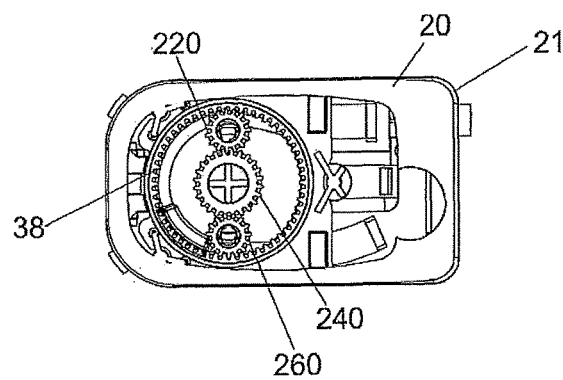
FIG. 8 shows a (horizontal) longitudinal section through the pump cartridge of FIG. 2 at a level of an epicyclic gear layer.

Finally, FIG. 8 shows the gear layer comprising the annulus outer gear ring 38 which specifies the position of the planet gears 220, 260 in relation to the rotation of the central or sun gear 240 which rotates through the coupling with a motor (not shown) in the pump module 6. The position of the central or sun gear 240 is stable in the center of the outer gear ring 38. The nominal gear teeth distance for good operation and lower gear ring friction is determined by the first and second bearing layers shown in the FIGS. 5 and 7 wherein the rollers 22, 24, 26 determine the exact respective teeth distance.

As to be noted from the aforementioned description, the planet roller 22 and the planet gear 220 commonly form a first integral rotary body, the central or sun roller 24 and the central or sun gear 240 commonly form a second integral rotary body, and the planet roller 26 and the planet gear 260 commonly form a third integral rotary body. These integral rotary bodies, wall portions of the lower and upper parts 20, 21 of the housing and further components comprise a slight conical shape in the same direction so as to achieve a slight V-shaped structure in cross-section, wherein the angle of the "V" defines a draft angle needed for demolding said components in case of a production of plastic. The mentioned slight conical or V-shaped structure can be suggestively to be seen from FIG. 4 but indicated in a more excessive way for a better illustration in FIG. 9.

Namely, the rollers 22, 24, 26 cannot be injection molded if they comprise a completely cylindrical form. While having no parting line at their sides, they need to have a draft angle of certain degrees for demolding, resulting in the bad effect that if the housing or barrel is cylindrical and the rollers are slightly conical, there would be a play or tolerance in one of the two bearing stages that would not be acceptable. Therefore, the aforementioned construction has a slightly V-shaped conical form so as to solve the aforementioned injection molding problem, under the consideration of the design rule that conical shapes in all rollers and the housing or barrel lead to a perfect rolling movement one over the other under the condition all conical lines intersect to and at one single point, as schematically shown in FIG. 9b. So, the housing or barrel, the sun or central roller 24 and the planet rollers 22, 26 are all of a slightly conical shape so that their side lines intersect to and at one point far away from the pump cartridge 4 since the draft angle is relatively small as it becomes clear from FIG. 9a. Whereas the planet rollers 22, 26 and their associated gears 220, 260 are inclined, the sun or central gear 240 is cylindrical so that the planet rollers 22, 26 and the central or sun gear 24 are rolling and gearing with each other. The inner walls of the housing or barrel are also slightly inclined to match the surface of the rollers 22, 24, 26 which also applies to the two outer bearing rings 30, 32 touching the rollers 22, 26 to enable bearing action.

Their resilient tubing 36 is preferably made of injection molded rubber or silicon, resulting in a production tolerance of only up to 1% which is a requirement to replace syringe pumps having an overall flow accuracy tolerance of about 2%. Also preferably, the resilient tubing 36 in its relaxed state does not have a round cross-section, but has a so-called angled-up-and-down or elliptical cross-section having a shape similar to an arrangement of two parentheses facing each other, i.e. "( )", resulting in a dramatic reduction of the power needed and, hence, of battery capacity and size.

Since the resilient tubing 36 is injection molded, preferably made of silicon injection molded and has a cross-section, as mentioned before, it can have different size and cross-section so as to annulate a pulsed infusion, to reduce the constancy index and the power needed, and to achieve a better pressure sensing and water tight barb connector attachment at the inlet 50 and the outlet 52 of the tubing 36. This is possible because the demolding process is done by blowing the tubing over an insert pin. Further, a particular type of material can be selected and the surface of the tubing can be treated in order to reduce the rolling friction.

According to the present invention, the tubing 36 is divided into four rotational sections or zones which are defined as being first to fourth zones A to D directly joining each other from the inlet 50 to the outlet 52 in downstream orientation which is defined by the direction of the flow of a fluid and is represented by the arrow A as shown in FIG. 10.

The first zone A being positioned downstream next to the inlet 50 and defining the most upstream zone is provided so that a planet roller 22 or 26 comes into engagement with the tubing 36 during movement along the first zone A. The first zone A extends along an angular distance (defining its length) with some degrees, preferably 5° to 15°, and is provided as a pressure management or safety stage. By coming into engagement with the tubing 36, the planet roller 22 or 26 starts to squeeze the tubing 36 so that fluid is encapsulated within the tubing 36 between this planet roller and a forerunner or leading planet roller. The first zone A assures safety on relay from the one planet roller (e.g. 22) to the next planet roller (e.g. 26), wherein there is no free flow due to the fact that at least one planet roller 22 or 26 is squeezing the tubing 36 anytime also in case the planet roller 22, 26 loose a perfect spacing in manufacturing. Also, at the first zone A which defines the initial section or stage of rotation, the cross-section of the tubing 36 is increased so that pressure is built up as represented by the aforementioned equation $$V+\Delta V_2/\Delta\varphi - \Delta V_1/\Delta\varphi = V + V \text{difference},$$

so as to level the pressure at the outlet 52 of the tubing 36 equal to the desired infusion pressure and to avoid hydroshock during disengagement of a planet roller 22 or 26 from the tubing 36. This is useful for subcutaneous infusions having a high downstream pressure. Since no pressure increase is required for intravenous infusion, the tubing 36 within the first zone A has a nominal or standard cross-section.

Due to the desire of having a constant infusion, it is wanted a constant infusion fluid flow (volume displacement $\Delta V$) per unit time ($\Delta t$) all along the rolling path of the planet rollers 22, 26 and, thus, along the whole tubing 36, when the planet rollers 22, 26 role with constant rotational speed $\omega = 2\pi/t$ along the tubing 36. In order to fulfill this, the volume $\Delta V$ created by the volume displacement action of the planet rollers 22, 26 is needed to be constant all along the rolling path of the planet rollers 22, 26 because of the following equation:

$$\text{Flow} = \Delta V/\Delta t = (\Delta V/\Delta\varphi) \cdot (\Delta\varphi/\Delta t) = (\Delta V/\Delta\varphi) \cdot C,$$

where $C = \Delta\varphi/\Delta t = \omega$ is a constant representing a constant rotational speed of the planet rollers 22, 26 in angle unit per time unit.

Therefore, the volume displacement action per rotational degrees of a planet roller 22, 26 is needed to be constant at any point of the infusion cycle, wherein in a two planet roller embodiment according to the present embodiment as described and illustrated here there are two cycles per revolution. The second to fourth zones B to D as described below assure that these needs are met.

The second zone B following the first zone A in downstream direction commences at a starting point where a planet roller 22 or 26 enters the second zone B at the same time when the leading planet roller just stops squeezing the tubing 36 and is going to be disengaged from the tubing 36 so that a flow communication is just going to come up. At that time, the following or trailing planet roller just enters the second zone B and takes relay of infusion. The tubing 36 in the second zone B has a higher cross-section than normal and in particular the third and fourth zones C and D. The cross-section of the second zone B is increased by an amount leading to an increase of volume which is at least equal to an increase of volume $\Delta Vd/\Delta\varphi$ in the fourth zone D resulting from the disengagement of the leading planet roller from the tubing 36. In other words, the increase of the volume due to a larger cross-section within the second zone B is at least equal to a void which is caused by the disengagement or release of the forerunner or leading planet roller from the tubing 36 when running along the fourth zone D. So, said void is compensated, and an equilibration of the flow of the fluid is achieved.

The third zone C following downstream the second zone B commences at a start point where the following or trailing planet roller enters the third zone C whereas at the same time the forerunner or leading planet roller has already been disengaged from the tubing 36 and, thus, does not touch the tubing 36 anymore. Preferably, the third zone C comprises a normal or nominal cross-section which is dimensioned so that a linear flow of the fluid through the third zone C is achieved in order to realize an infusion at a standard rate $\Delta V/\Delta\varphi$. According to the embodiment as illustrated in FIG. 10, the sum of the angular distance of the second zone B and of the angular distance of the third zone C is in total 180° for the embodiment having two planet rollers 22, 26 which are arranged diametrically opposite to the center or sun roller 24 as described above with reference to the FIGS. 3 to 8, In case of an alternative embodiment (not shown) having three planet rollers which are spaced from the center or sun roller by the same radial distance wherein two neighboring planet rollers each are spaced from each other by an angular distance of 120°, the sum of the angular distance of the second zone B and of the angular distance of the third zone C is in total 120°.

The fourth and last zone D following downstream the third zone C and being the most downstream zone is adapted for a disengagement of the planet rollers 22, 26 from the tubing 36 during movement along the fourth zone D. Namely, the fourth zone D is provided for a control release of the forerunning or leading planet roller from the tubing 36 wherein according to the illustrated embodiment a controlled release is achieved due to an increase of the radius of curvature to $r+\Delta r/\Delta\varphi$. In particular, the increase of the radius can follow an asymptotic line or a portion of a spiral. This controlled curvature defines an arc of disengagement which depends on the capability to increase the cross section of the tubing 36 in the second zone B, and cannot be minimal since then a large bubble would be needed in the second zone B, resulting in difficulties for the production.

The volume void created by the disengagement or release of a planet roller 22 or 26 from the tubing 36 is used for a determination or calculation of the volume of the second zone B having an increased cross-section of the tubing 36. In other words, in view of $+\Delta Vd/\Delta\varphi$, the increase of the volume of the second zone B is calculated to be equal with the volume void as additionally created in the fourth zone D due to the disengagement or release of the planet roller from the tubing 36. So, the volume void created per $\Delta\varphi$ according to $-Vd/\Delta\varphi$ within the fourth zone D is equally compensated by a so-called over-infusion caused by an increased cross-section of the tubing within the second zone B according to $+\Delta Vb/\Delta\varphi$, with $$\Delta Vb/\Delta\varphi = \Delta Vd/\Delta\varphi$$

and therefore $$(\Delta V/\Delta\varphi + \Delta Vb/\Delta\varphi) - (\Delta Vd/\Delta\varphi) = \Delta V/\Delta\varphi$$

resulting in a constant flow at any angular position $\varphi$ due to an equilibration of the flow of the fluid, so that for each point in the fourth zone D there is a compensating pendant point in the second zone B.

So, there is a correlation of the curvature of the tubing 36 with the increase of the cross-section of an upstream portion of the tubing 36 corresponding to the second zone B so that additional volume of the tubing 36 created by disengagement or release of the planet roller from the tubing 36 within the fourth zone D is compensated by additional volume provided by a larger cross-section of the tubing 36 along the second zone B. According to the embodiment as illustrated in FIG. 10, the sum of the angular distance of the third zone C and of the angular distance of the fourth zone D is in total 180° for the embodiment having two planet rollers 22, 26 which are arranged diametrically opposite to the center or sun roller 24 as described above with reference to FIGS. 3 to 8. In case of an alternative embodiment (not shown) having three planet rollers which are spaced from the center or sun roller by the same ratio distance wherein two neighboring planet rollers each are spaced from each other by an annular distance of 120°, the sum of the angular distance of the third zone C and of the angular distance of the fourth zone D is in total 120°

Hence, the increased volume per rotational angle is delivered by the trailing planet roller moving along the second zone B after a release or disengagement of the leading planet roller from the tubing 36 has started in the fourth zone D. As a result, the trailing planet roller sustains the required flow of the fluid.

So, the flow $(\Delta V/\Delta\varphi)\cdot\omega$ in front of a planet roller 22 or 26 in case only a single planet roller engages the tubing 36 in the third zone C must be equal and constant to the flow $(\Delta V_2/\Delta\varphi + \Delta V_1/\Delta\varphi)\cdot\omega$ in case of an engagement of two planet rollers 22, 26 in the second zone B and the fourth zone D, respectively. Since $(\Delta V_1/\Delta\varphi)$ caused by the forerunning or leading planet roller (e.g. 22) becomes negative due to suction in the fourth zone D, $\Delta V_2/\Delta\varphi$ created by the following or trading planet roller (e.g. 26) running along the second zone B needs to be positive so as to balance the sum of $\Delta V_1/\Delta\varphi$ and $\Delta V_2/\Delta\varphi$ to be equal to $\Delta V/\Delta\varphi$ within the third zone C along which only one planet roller 22 or 26 is running at the same time. Accordingly, as already described above, if the cross-section of the tubing 36 within the fourth zone D is equal to the cross-section of the tubing 36 within the third zone C, the cross-section of the tubing 36 within the second zone B must be bigger in order to compensate the loss. Flow a numerical emulators available on the market and known in the prior art can be used for calculation of the void and compensation. If the planet rollers do not have a minimal diameter resulting in a late decompression and opening of the tubing 36 within the fourth zone D, a suction from the outlet 52 before opening may be noticed when the leading planet roller is going to be disengaged or released from the tubing 36, while a flow from behind cannot take place yet. This can be corrected by the provision of an express flow opening without perturbing a controlled disengagement or release of the planet roller within the fourth zone D, which can be realized by the provision of a gully (not shown) inside the resilient tubing starting at the beginning of the fourth zone D in order to suddenly open the flow as sustained from the trailing planet roller. With a sudden opening of the flow, instead of a gully recess within the tubing, the provision of a partial width or total width step 48 as further shown in FIG. 3, wherein the "Π"-shaped cross-section of the aforementioned cavity of the lower part 21 of the housing becomes deeper in radial direction within the fourth zone D, in order to realize an abrupt retreat of the wall portion 40 for a depth as much as needed for just opening the flow from behind the tubing 36 is also possible with the same effect, wherein the rest of the fourth zone D is provided for a controlled disengagement of the planet rollers from the tubing 36 in association with the increased volume of the second zone B as described above.

The angular distance (defining the length) of the second zone B is preferably equal to the angular distance of the fourth zone D and may be preferably 20° to 60° for a realistic controlled release or disengagement of the leading planet roller from the tubing 36 within the fourth zone D without any flow perturbation. An increase of the angular distance would make a smaller zone increase per degree, and a decrease of the angular distance would result in the provision of a smaller mechanism. So, the construction depends on the use specifications, wherein all possibilities from a few degrees to 180° might give a constant flow. The sum of the angular distances of all the four sections A to D must be equal to or less than 360°.

Whereas the first zone A is provided so that the planet rollers 22, 26 come into engagement with the tubing 36 during movement along the first zone A and the fourth zone D is provided so that the planet rollers 22, 26 are disengaged from the tubing 36 during movement along the fourth zone D, the second and third zones B and C are provided so that at least planet roller 22 or 26 remains in engagement with the tubing 36 during movement along the second and third zones B and C.

In the following there is a description of how the aforementioned construction according to a preferred embodiment of the present invention works:

At the same time when a previous forerunning or leading planet roller is disengaged or released from the tubing 36 at the end of the fourth zone D, a following or trailing planet roller (e.g. 22) is just going to enter the third zone C so that the latter planet roller is relayed as a new forerunner or leading planet roller which at that time is the only planet roller touching and, thus, squeezing the tubing 36 as long as it moves along the third zone C. So, a constant infusion $\Delta V/\Delta \varphi$ is provided. Before the latter mentioned planet roller being now the leading planet roller reaches the end portion of the third zone C, the next following upstream planet roller (e.g. 26) enters the first zone A and is going to touch and squeeze the tubing 36 so that between these two neighboring planet rollers 22, 26 a standard or nominal volume is encapsulated within the tubing 36. The encapsulation of a volume having the same repeatable amount assures the desired accuracy of infusion. This is assured by fixing the tubing 36 to the wall portion 40 due to a cooperation of the hooks 42 at the tubing 36 and the corresponding recesses 44 in the wall portion 40.

Preferably, the cross-section of the tubing 36 in the first zone A may be larger than the cross-section of the third zone C, wherein in particular the cross-section of the tubing 36 in the first zone A decreases from a large amount at the beginning of the first zone A to a normal or nominal amount at the end of the first zone A corresponding to the normal or nominal amount of the cross-section of the tubing 36 in the third zone C. So, within the first zone A an increased infusion pressure may be built up which is higher than the pressure within the infusion line corresponding to the atmospheric pressure, resulting in that within the first zone A the tubing 36 is inflated by $$V+\Delta V_2/\Delta \varphi - \Delta V_1/\Delta \varphi = V + V \text{difference},$$

Said increased infusion pressure may be lower or zero for intravenous infusions and higher for subcutaneous infusions. As a result, after disengagement or release of the leading planet roller from the tubing 36 within the fourth zone D the pressure at that point can be equal to the downstream pressure, and therefore the flow of fluid out of the encapsulated volume is essentially even. So, there is no backflow of fluid into the resilient tubing 36 since pressures in front of and behind said planet roller are made essentially equal.

As already mentioned above, in the described embodiment having two planet rollers 22, 26, at the same time when the trailing upstream planet roller exits the first zone A and enters the second zone B, the forerunner or leading planet roller exits the third zone C and enters the fourth zone D and, hence, starts to be released or disengaged from the tubing 36. Due to the release or disengagement from the tubing 36, a so-called communication arises and is opened under the leading planet roller which results in that the optional high pressure of the fluid as created in the first zone A is immediately released. This leads to an equilibration of the pressures so that there is no perturbation of the pressure and flow which would otherwise result from that a higher infusion pressure could make the fluid come back and inflate the resilient tubing and create a momentary flow negative pulse.

During the simultaneous movement along the second and fourth zones B and D, each partial release of the forerunning or leading planet roller within the fourth zone D creates a void, and each partial rotation of the upstream trailing planet roller within the second zone B creates an over-infusion which, however, are essentially equilibrated with each other so that the infusion is maintained essentially constant by compensation of flow differences due to the special configuration of the second zone B as explained above.

Figure 11:
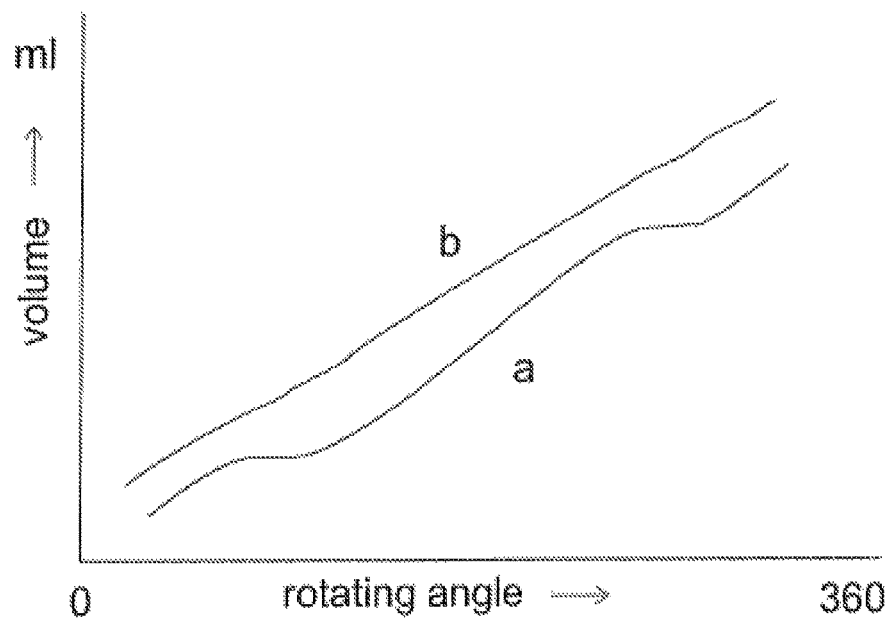
FIG. 11 schematically shows a graph including a curve "a" representing the situation without any correction and a curve "b" representing a pulseless situation after a correction.

FIG. 11 shows the effect of the pulseless correction as described above as a chart of weight vs. the rotating angle of the planet rollers 22, 26 over the complete angular range of 0° to 360°, wherein the curve "a" represents the situation before the correction and shows a pulse for each of the two infusion cycles per rotation at the two roller exchange points where both the planet rollers are still engaged with the tubing 36 simultaneously, and curve "b" shows a pulseless situation after correction due to the measures as described above and, hence, defines an essentially straight line.

Figure 12:
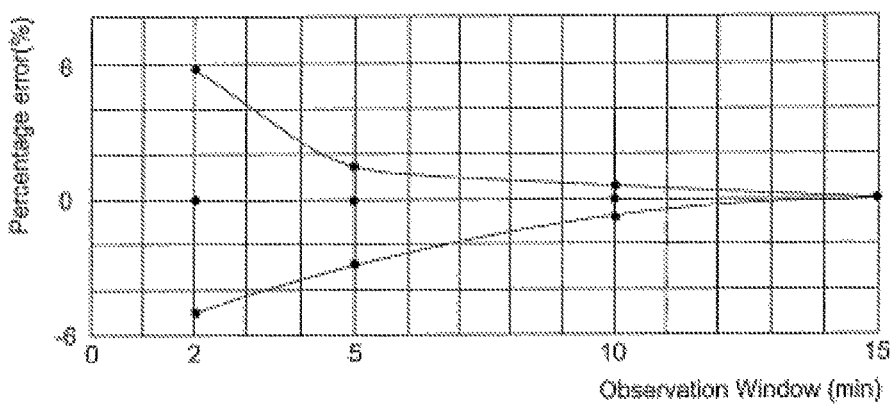
FIG. 12 schematically shows a trumpet curve according to the IEC 60601-2-24 Standard.

FIG. 12 shows a trumpet curve with the aforementioned corrections of linearity of flow, but without the use of any additional electronic correction means, so that this is matching the best syringe pumps, wherein the constancy index as defined above is below 2 min. so as to match the short live drug infusion needs of today. The trumpet curve is a graph which is well-known in the field of infusion and is based on a statistical measurement wherein as to further details reference is made to the International Standard IEC 60601-2-24.

It is known in the art that correction of flow can also be done by temporarily acceleration of the motor speed at so-called under infusion (pulse) angles of rotation. Namely, as shown from the aforementioned equation flow rate=$(\Delta V/\Delta \varphi) \cdot (\Delta \varphi/\Delta t)$, a decrease of $\Delta V$ at a predetermined angle $\varphi$ can be compensated by an increased $\Delta \varphi/\Delta t$. However, commercially this solution in the 90s did not have success as patients were complaining that such a pump would be not a good pump having irregular flow as erroneously perceived from an assumed motor irregularity sound. A slight motor acceleration and deceleration cannot be perceived if it is done after a mechanical flow correction as described above so that in such a case commercialization will be no problem anymore.

According the present invention, there is provided a rotary peristaltic pump mechanism with an augmented volume section of the tubing 36 within the second zone B and eventually a sudden increase of the depth due to the step 48 within the fourth zone D opening for flow correction associated preferably with (not equal but) different timer settings per motor step at low rates. Such a step is defined as a so-called motor positioning feedback step wherein in a preferred embodiment there are about 80 steps per half rotation corresponding to a roller relay section of 180°, wherein an infusion rate determines a normally constant interrupt time per step. If the aforementioned mechanical correction is not perfect, from a measured volume to step graph it is to be observed that portions of the curve being above a rate line represent an infusion requiring a smaller timer interrupt, and portions being below the rate line represent an infusion requiring a smaller time interrupt, wherein an electronic correction look-up table per step of infusion is defined and determines the timing for each step in order to completely correct the linearity of flow. With such small differences in timing, an additional electronic correction is not perceptible anymore by the users.

The constancy index is dramatically decreased by the aforementioned linearity of infusion, and in combination with an injection molded manufacturing of the tubing a production tolerance (accuracy) of at most 2% can be achieved, which makes a peristaltic pump as good as a syringe pump in particular for biological drugs, insulin infusion as well as catecholamines, heparin and nitrates which need a short term accuracy with low constancy index and a high accuracy. In particular for biological drugs and insulin, the pump mechanism can be provided with a barrel diameter of only 10 mm, allowing an extremely small size in combination with multilayer reservoirs (e.g. for oxygen and $CO_2$ barriers) (i.e. comprising polypropylene material with low temperature outside and high temperature inside and including binding material like TPE or other barrier materials like polytetrafluoroethylene (TPFE) or polyvinylidene chloride (PVDC) or ethylenevinyl alcohol (EVOH) as known e.g. from U.S. Pat. No. 9,162,025 B2) in which a pre-filled medication can be stored for many years. So, the provision of an overall square inch pump is possible. Therefore, the present technology can be used for bolus high volume injectors. For biological fluids and insulin, low volumes and usually ultra-low rates are needed so that a complete patch pump with the aforementioned consumable pump cartridge 4 as infusion mechanism (further comprising a teflon (PTFE) infusion needle as known in the prior art) can be provided without a conventional motor, but a driving saw tooth gear directly connected with the combined central or sun roller and gear 24, 240, wherein such a driving gear rotates tooth by tooth through a ratchet which advances the rotation but blocks a back rotation due to the force of a spring loaded for expansion which spring may comprise a thermoshrinkable shape memory alloy element such as a nitinol wire as known from U.S. Pat. No. 6,656,159 B2. Such a shape memory wire shrinks under electrical power and moves one gear tooth resulting in rotation of the central or sun roller by some angles, and, when electrical power is removed, it expands by the spring force to a standby position for engaging the next tooth.

For parenteral nutrition, a pre-filled reservoir as known in the art includes three or more compartments which are pre-filled or compounded with nutrient which can be mixed by hand action so as to break the sealing between the compartments before use. For improved contamination avoidance, self-administration of the contents by untrained patients is possible as follows:

The pre-filled reservoir comprises three or more pre-filled compartments including sealing strips there between which can be opened by hand action for mixing the contents. The pump cartridge can be fluidly connected to the reservoir through a three-way inlet valve in order to avoid the risk of an upstream contamination of a prior art spike connection. Also, at the distant end of the downstream tube there is provided an anti-contamination Luer connector (as disclosed in EP 2 756 863 A1 or US 2014/0207118 A1), wherein at first a priming by gravity occurs after opening said valve by hand action wherein the flow stops at a hydrophobic membrane of the connector, and then the user removes a cap of his central venous catheter from said connector assembly and rejects both connected caps together and thereafter makes the required connection without touching any part of the catheter other than the back of the connector and without any risk of contamination at both ends of the infusion line. Thereafter, a driving controller for the pump is coupled to the system for infusion. The reservoir, in particular at one of its edges, comprises an RFID label in which the nutrient contents are stored. The nutrient contents and their volume are recorded by the pump and sent wirelessly to a distant server where they are stored in a data base and output to medical personnel in view of the dates for a nutritional review. Further, the pre-filled reservoir may be provided with internal microstriations which do not allow self-sealing of the plastic sides by suction, so that such a reservoir can be used even at horizontal placement or in an ambulatory way without the risk of triggering upstream occlusion alarms.

Figure 13:
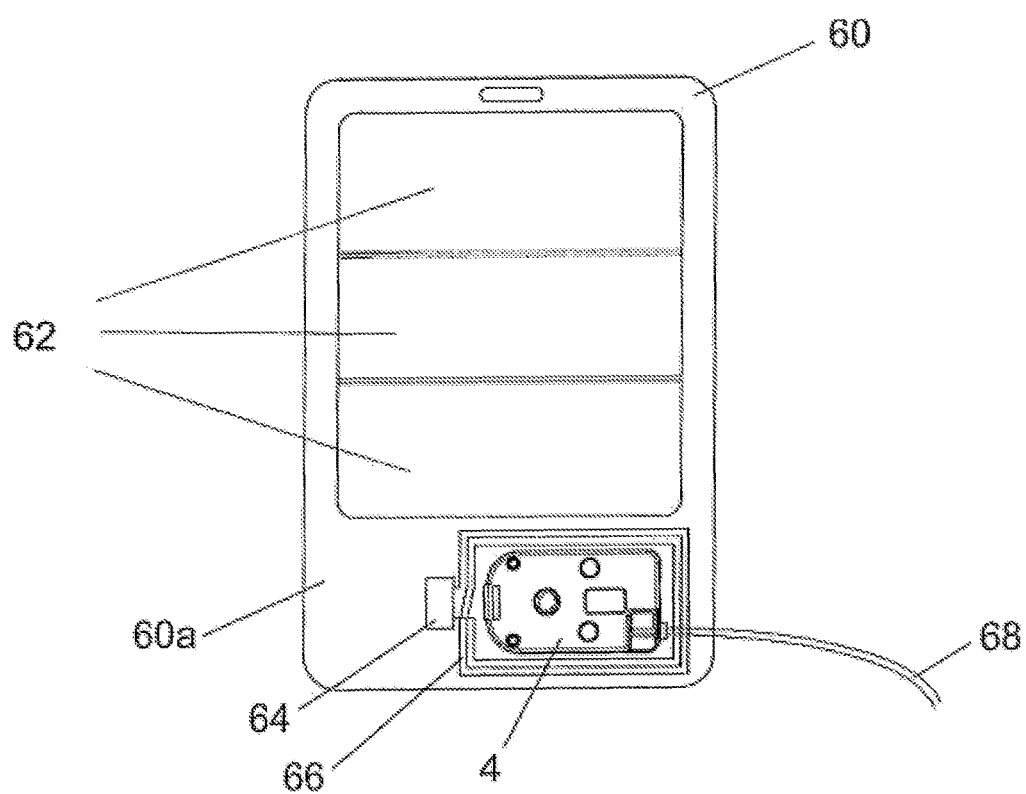
FIG. 13 schematically shows an integrated arrangement comprising a medication reservoir, a pump cartridge and an RFID label according to a preferred embodiment.

As an example, in FIG. 13 there is shown a pre-filled medication reservoir 60 including three compartments or chambers 62. As further to be seen from FIG. 13, an RFID label 64 is positioned at the lower edge region 60a of the medication reservoir 60. Preferably, the label 64 may be welded into the material of the medication reservoir 60 between upper and lower foils. In the illustrated embodiment according to FIG. 13, a pump cartridge 4 is also arranged at the lower edge portion 60a of the medication reservoir 60. In contrast to what is shown in the FIGS. 1 to 3, a spike is missing since the inlet of the rotary peristaltic pump mechanism of the pump cartridge 4 is in direct fluid communication with the medication reservoir 60. An antenna 66 to which the label 64 is coupled is provided as a wire pattern surrounding the pump cartridge 4 so that in any case it is assured that a label reader included in a pump module 6 or a pump controller can read the label contents which, by the way, are also printed on the medication reservoir 60. Moreover, FIG. 13 shows a downstream tube 68 which is coupled to the outlet of the rotary peristaltic pump mechanism within the pump cartridge 4 and extends to an anti-contamination luer connector (not shown) attached to a patient's catheter connector (not shown as well).

What is claimed is:

1. An infusion pump device, comprising:
a peristaltic pump means including,
   a stationary flexible tubing which has an inlet and an outlet and is provided to accommodate a fluid flowing in downstream direction from the inlet to the outlet, and
   at least two engagement elements which are spaced from each other by a predetermined constant distance and provided to locally engage with the tubing and to be repeatedly moved along the tubing in downstream direction so as to locally squeeze the tubing for a pump action during movement of the engagement elements along the tubing and to encapsulate a volume of the tubing between two neighboring engagement elements, wherein:
   the tubing comprises first to fourth zones directly joining each other in downstream direction,
   the first zone being the most upstream zone is provided so that an engagement element comes into engagement with the tubing during movement along the first zone,
   the second and third zones are provided so that an engagement element remains in engagement with the tubing during movement along the second and third zones,
   the fourth zone being the most downstream zone is provided so that an engagement element is disengaged from the tubing during movement along the fourth zone,
   the second zone, following the first zone in downstream direction, commences at a starting point where an engagement element enters the second zone at the same time when in the fourth zone a neighboring leading engagement element just stops squeezing the tubing and is going to be disengaged from the tubing so that a flow communication is just going to come up,
   the third zone, following downstream the second zone, commences at a start point where an engagement element enters the third zone whereas at the same time a neighboring leading engagement element has already been disengaged from the tubing and, thus, does not touch the tubing anymore,
   the length of each of the zones is shorter than the distance between the two neighboring engagement elements,
   the sum of the lengths of the second and third zones is equal to the distance between the two neighboring engagement elements,
   the length of the second zone is equal to the length of the fourth zone, and
   the cross-section of the second zone is larger than the cross-section of the third zone by an amount leading to an increase of volume which is at least equal to an increase of volume displaced in the fourth zone resulting from the disengagement of an engagement element from the tubing.

2. The device according to claim 1, wherein the flexible tubing is resilient.

3. The device according to claim 1, wherein the sum of the lengths of the third and fourth zones is equal to the distance between the two neighboring engagement elements.

4. The device according to claim 1, wherein the length of the third zone is longer than the length of the first zone and/or of the second zone and/or of the fourth zone.

5. The device according to claim 1, wherein the cross-section of the first zone is larger than the cross-section of the third zone.

6. The device according to claim 1, further comprising a housing accommodating the peristaltic pump means, and fixing means for fixing the tubing to the housing so as to prevent movement of the tubing relative to the housing.

7. The device according to claim 1, wherein the peristaltic pump means is a rotary peristaltic pump means comprising a rotor which is provided with the engagement elements wherein the tubing comprises a bent portion having an essentially part-cycle form, and wherein the length of the zones is represented by an angular distance.

8. The device according to claim 7, wherein the angular distance of the first zone is up to 15°.

9. The device according to claim 7, wherein the angular distance of the second zone is 20° to 60°.

10. The device according to claim 7, comprising two engagement elements which are arranged essentially diametrically opposite to a rotary axis of the rotor, wherein the sum of the angular distances of the second and third zones is equal to 180°.

11. The device according to claim 7, comprising three engagement elements which are spaced from a rotary axis of the rotor by the same radial distance wherein two neighboring engagement elements each are spaced from each other by an angular distance of 120°, wherein the sum of the angular distances of the second and third zones is equal to 120°.

12. The device according to claim 7, wherein the engagement elements are provided as engagement rollers.

13. The device according to claim 12, wherein the rotor comprises a central roller which is in frictional engagement with the engagement rollers.

14. The device according to claim 13, further comprising a housing including a bent wall portion which supports at least a portion of the tubing and provides the tubing with a curved shape, wherein the engagement rollers, the central roller, an outer ring and the bent wall portion comprise a conical shape in the same direction.

15. The device according to claim 1, further comprising a shutter means which is adapted to be optionally placed either in a first position or in a second position, wherein the shutter means in its first position allows the tubing to be squeezed by an engagement element for a pumping action and in its second position prevents the tubing from squeezing by an engagement element so as to let air or fluid pass through the tubing.

16. The device according to claim 1, further comprising a controlling means for controlling the movement of the engagement elements so as to correct the position and speed of the engagement elements if needed.

* * * * *